United States Patent [19]

Laroco

[11] Patent Number: 4,899,749
[45] Date of Patent: Feb. 13, 1990

[54] THERMAL VASCULAR DILATING DEVICE AND METHOD

[76] Inventor: Elizabeth Laroco, 714 Lancing Rd., Woodbury, N.J. 08096

[21] Appl. No.: 267,363

[22] Filed: Nov. 4, 1988

[51] Int. Cl.$^4$ .............................................. A61F 7/02
[52] U.S. Cl. .................................. 128/402; 383/901; 606/27
[58] Field of Search .............. 128/402, 403, 379, 380, 128/341, 303.12, 399, 24.1, 82.1, 400; 383/901; 62/259.3, 530

[56] References Cited

U.S. PATENT DOCUMENTS

| | | | |
|---|---|---|---|
| 543,177 | 7/1895 | Daly | 128/402 |
| 1,775,442 | 9/1930 | Sarason | 128/402 |
| 2,783,807 | 3/1957 | Duffield | 150/2.4 |
| 3,463,161 | 8/1969 | Andrassy | 128/402 |
| 3,506,013 | 4/1970 | Zdenek | 128/402 |
| 3,678,936 | 7/1972 | McCormick | 128/402 |
| 3,785,375 | 1/1974 | Lipson | 128/82.1 |
| 4,071,031 | 1/1978 | Lowman | 128/402 |
| 4,107,509 | 8/1978 | Scher et al. | 128/379 |
| 4,259,961 | 4/1981 | Hood, III | 128/400 |
| 4,344,303 | 8/1982 | Kelly, Jr. | 62/530 |
| 4,347,848 | 9/1982 | Hubbard et al. | 128/402 |
| 4,356,709 | 11/1982 | Alexander | 62/530 |
| 4,527,566 | 7/1985 | Abare | 128/402 |
| 4,530,220 | 7/1985 | Nambu et al. | 62/530 |
| 4,736,088 | 4/1988 | Bart | 128/402 |
| 4,747,409 | 5/1988 | Silen | 128/402 |

FOREIGN PATENT DOCUMENTS 1064250  4/1986  Japan .................. 126/204

*Primary Examiner*—Edward M. Coven
*Assistant Examiner*—Mark J. Graham
*Attorney, Agent, or Firm*—Thomas A. Lennox

[57] ABSTRACT

A thermal vascular dilating device including a cylindrical shaped water tight container with the center opening sufficient to allow the arm to fit through preferably with a lengthwise cut held together with VELCRO straps and a length long enough to interfit over the hand with a VELCRO strap closure to fold the device over the hand with a threaded spout and cap opening for filling the container with warm water.

11 Claims, 2 Drawing Sheets

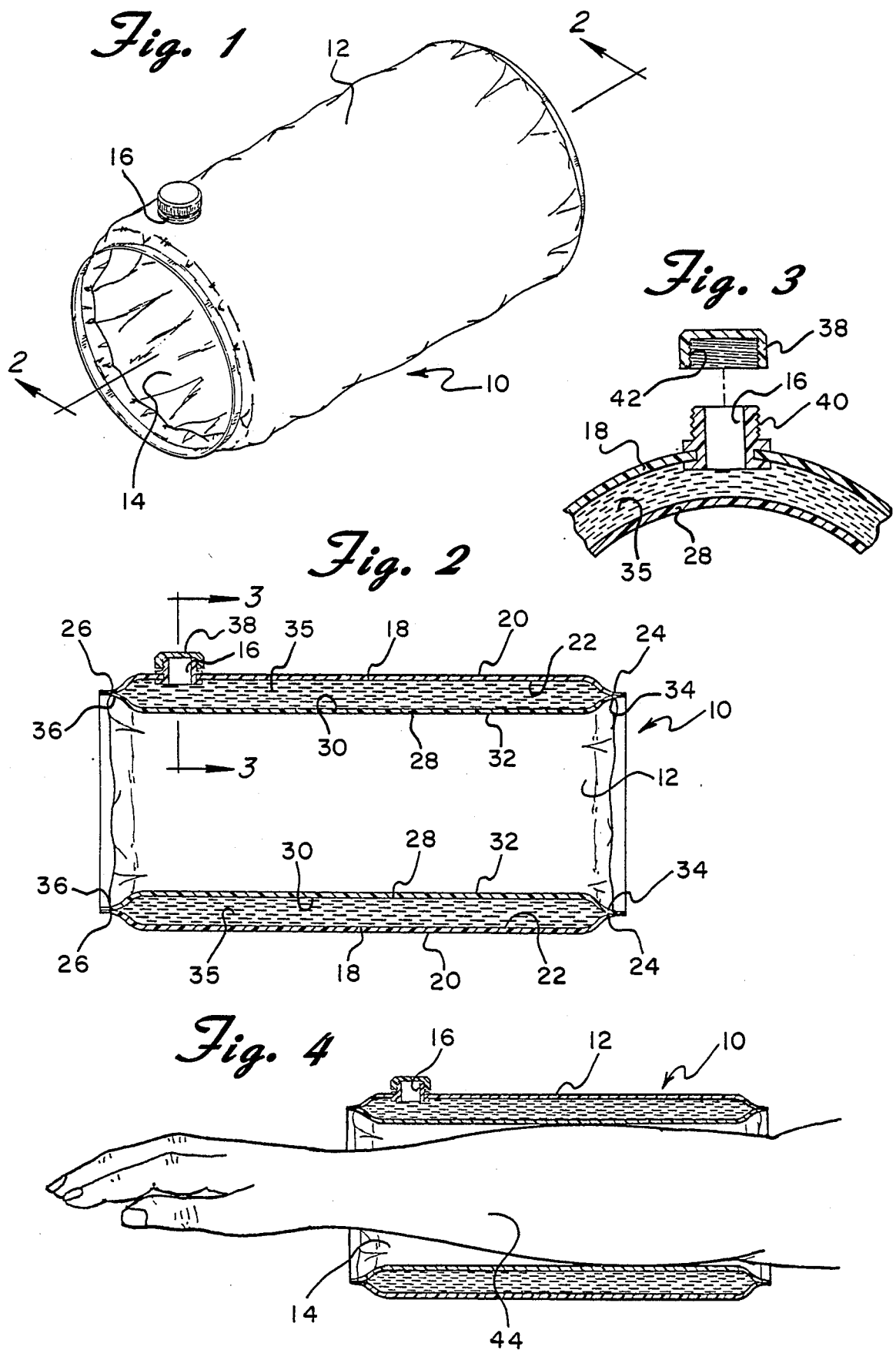

THERMAL VASCULAR DILATING DEVICE AND METHOD

BACKGROUND OF THE INVENTION

This invention involves a device for dilating the blood vessels of a person's extremity by a thermal treatment.

Intravenous therapy, commonly known as IV therapy is a common practice carried out in hospitals as well as in clinics or even in Doctor's offices. Venipuncture requires the insertion of sampling and infusion cannulas in the veins of the extremities, typically the arms or hands of adults but also the feet of infants. Venipuncture is used not only to collect blood samples, but also for the infusion of various medicines. Many patients have vessels that are not perfect for puncture and even the most trained specialist has difficulty with some patients. Age is a significant factor as older persons as well as the youngest infants are generally more difficult patients for the administration of venipuncture. Some patients have diseases that effect the veins making the procedure more difficult. Heat pads are commonly used to heat the arm before venipuncture in order to increase the blood flow in that area to make the veins more accessible. Unfortunately, heating pads are not adapted for this application and they do not surround the arm and easily slip off and lose contact with the extremity causing poor heat conductance. In addition, temperature control is difficult as it is desired to maintain a stable temperature in the range of about 30 degrees C. and to about 50 degrees C. It is preferred that the temperature of the arm be about 110 degrees F.

There is a clear need for an effective thermal vascular dilating device that is portable, simple to use, can be reused, and yet can be discarded after multiple use with no great loss. None of the prior devices satisfy this need or attain the objects described hereinbelow.

SUMMARY OF THE INVENTION

It is an object of this invention to provide a portable thermal vascular dilating device which requires no electrical power and can be used by untrained personnel. Inasmuch as hot tap water at 110 degrees F. is available in most hospitals, there is little danger that a person might be burned using the device of the present invention.

It is an additional object of the present invention to provide a thermal vascular dilating device which can utilize any flowable material that can retain the heat and is specifically effective with warm water.

It is a further object of the present invention to provide a thermal vascular dilating device which can be easily slipped over the extremity to dilate the veins and then be slipped off for venipuncture procedures.

It is a specific object of the present invention to provide a thermal vascular dilating device which interfits over an extremity such as an arm, covering and heating not only the arm but also the hand to facilitate and accelerate the warming effect.

The invention is a thermal vascular dilating device to fit over a person's extremity, generally an arm. The dilating device includes a heat retaining flowable material tight container that includes a cylindrical shaped flexible outside wall having an inner surface, an outer surface, and two circular end edges and a cylindrical shaped flexible inside wall having an inner surface, an outer surface, and two circular end edges, the inside wall nested inside the outside wall. The container further includes sealing means to seal the adjacent end edges of the inside and outside walls together forming a cylindrical cavity between the outer surface of the inside wall and the inner surface of the outside wall. The composition and the thickness of the walls are sufficient to allow heat conduction through the walls sufficient to dilate the vascular system of an extremity when inserted into the cavity inside the inside wall. The device further includes an opening means providing an opening into the cavity to allow it to be filled with warm heat retaining flowable material, sealably closed, opened, and emptied.

It is preferred that the opening means be through the outside wall and more preferably be a threaded spout and screw cap. It is preferred that the walls be of a polymeric plastic film and more preferred that the film be cloth reinforced. It is most preferred that the walls be of an elastomeric polymer. It is preferred that the container have a lengthwise cut from end to end and that adjacent edges of each wall be sealably attached to form a sealed cylindrical cavity with a lengthwise separation, and that the device further include a closure means to hold the lengthwise edges together along the cut. It is also preferred that the closure means include straps with VELCRO closures to attach the straps across the separation.

The invention is also a method of thermally dilating the vascular system of a person's extremity. The method includes providing a dilating device that includes a heat retaining flowable material tight container. The container includes a cylindrical shaped flexible outside wall having an inner surface, an outer surface, and two circular end edges, and a cylindrical shaped flexible inside wall having an inner surface, an outer surface, and two circular end edges, the inside wall nested inside the outside wall. The container further includes sealing means to seal the adjacent end edges of the inside and outside walls forming a cylindrical cavity between the outer surface of the inside wall and the inner surface of the outside wall. The composition and the thickness of the walls are sufficient to allow heat conduction through the walls. The device further includes an opening means providing a closable opening into the cavity. The method further includes filling the device with warm heat retaining flowable material, preferably a liquid, and more preferably water, expelling air from the cavity out the opening means and closing the opening means. The method further includes slipping the device over the extremity, and waiting a sufficient time for the vascular system to dilate. The method further includes removing the device to expose the access to the vascular system. It is preferred that the method further include wrapping the person's hand with a warm heat insulating fabric such as a warm wet towel. It is more preferred that the length of the container be sufficient to cover the extremity, such as from the elbow over the hand, where the end may be closed over the hand.

BRIEF DESCRIPTION OF THE DRAWINGS

FIG. 1 is a perspective view of a thermal vascular dilating device of the present invention.

FIG. 2 is a cross-sectional view taken along lines 2—2 of FIG. 1.

FIG. 3 is an expanded partial cross-sectional view taken along lines 3—3 of FIG. 2.

FIG. 4 is a vertical cross-sectional view of the device illustrated in FIG. 1 interfitted over a person's arm.

DESCRIPTION OF PREFERRED EMBODIMENTS

Figure 5:
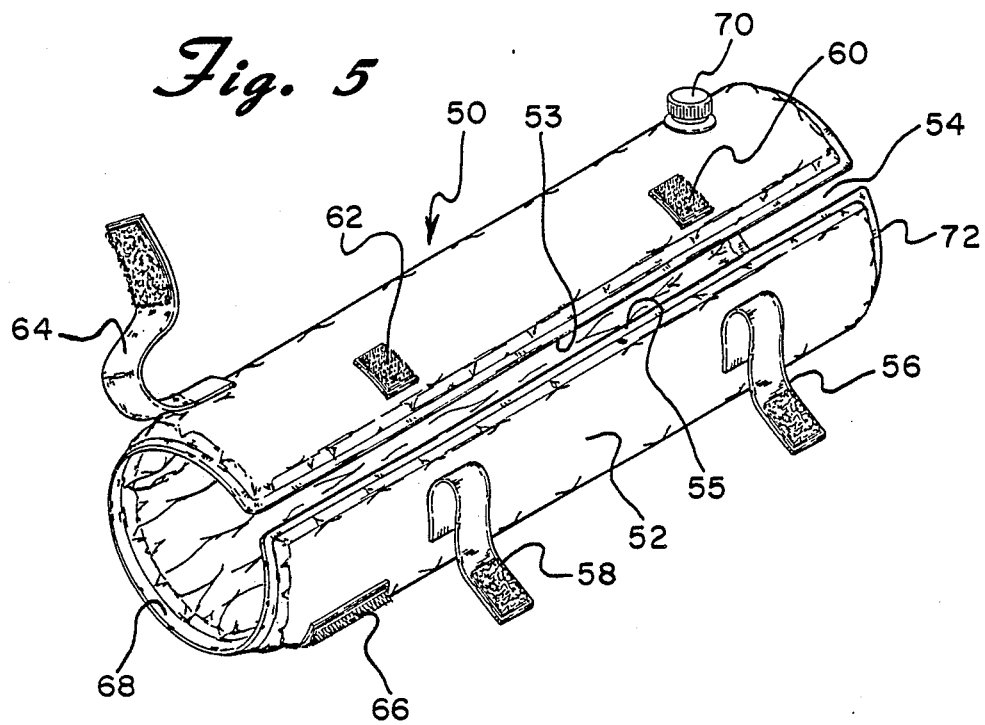
FIG. 5 is a perspective view of a second embodiment of the present invention.

Thermal vascular dilating device 10 is illustrated in FIG. 1 including a cylindrical container 12 with center opening 14, opening the length of the container with capped spout opening 16 opening into the container.

In FIG. 2, dilating device 10 is pictured constructed of outside cylindrical flexible wall 18 with outer surface 20 and inner surface 22 having circular ends 24 and 26. The other portion of container 12 is inside cylindrical wall 28 which is nested inside outside wall 18. Inside wall 28 has outer surface 30 and inner surface 32 as well as circular ends 34 and 36. The walls are constructed of a polymeric plastic preferably an elastomer, such as rubber. It is preferably fabric reinforced for durability. Ends 24 and 34 are sealed together as are ends 26 and 36 to form a cylindrical cavity 35 filled with warm water. Spout opening 16 is closed with cap 38 more fully illustrated in FIG. 3. Spout opening 16 includes male threads 40 on the outside surface which are threadably engaged with female threads 42 on the inside surface of cap 38. In FIG. 4, dilating device 10 is utilized by slipping cylindrical container 12, which is about 10 to 12 inches long, over arm 44 which interfits into and through opening 14. The opening lengthwise through the container is about four to six inches in diameter.

Figure 6:
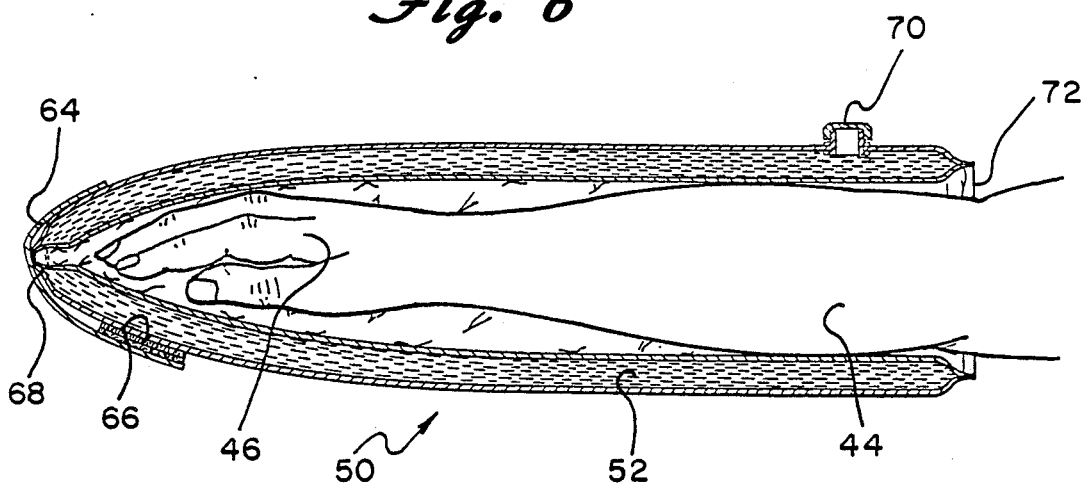
FIG. 6 is a vertical cross-sectional view of the device illustrated in FIG. 5 interfitted over a person's arm.

In FIG. 5, a second embodiment of the invention is illustrated in the form of thermal vascular dilating device 50. Device 50 includes cylindrical container 52 which is constructed essentially identically with that of container 12 except, that it is about 18 to 20 inches long and a lengthwise slot opening 54 is provided. Lengthwise edges 53 and 55 are sealably connected in the same fashion as edges 24 to 34 and 26 to 36 in device 10. Thus, a cylindrical cavity fillable with warm water is produced inside container 52. Straps 56 and 58 with VELCRO fasteners on the ends are attached on one side of slot opening 54 and are attachable to VELCRO fasteners 60 and 62 on the opposite side of slot opening 54 to close device 50 after the arm is inserted into the opening inside the cylindrical container. Strap 64 with a VELCRO fastener extends across and attached to VELCRO fastener 66 to close circular end 68 to reduce heat loss during dilation. Although VELCRO fasteners are used throughout, any fabric hook and loop fastening device is preferred. In FIG. 6, device 50 is shown on arm 44 also enclosing hand 46 by closing off end 68 with strap 64 to concentrate the heat conduction. Cap spout 70 is used to fill an empty cylindrical container 52. Open circular end 72 is essentially closed off by the arm to prevent heat loss in that direction.

In practice, the device is filled with hot tap water with about 110 degrees F. Air is expelled from the cavity through the spout opening and the cap is securely screwed on. The cylinder is slipped over the arm making sure that it is not too tight to restrict blood flow. Various sizes may be necessary in order to provide the best contact against the arm. For that reason, the embodiment illustrated in FIGS. 5 and 6 is preferred as there is an adjustment to account for different size arms. For best results, either the device illustrated in FIG. 6 is used or when the device illustrated in FIG. 1 is used, it is best to wrap the hand with a towel to prevent heat loss from the skin. Generally, the cylinder and the towel are left on the arm for about 10 to 15 minutes. The cylinder and towel are removed to proceed with normal venipuncture procedures. After use the entire device is cleansed with a disinfectant.

While this invention has been described with reference to the specific embodiments disclosed herein, it is not confined to the details set forth and the patent is intended to include modifications and changes which may come within and extend from the following claims.

I claim:

1. A thermal vascular dilating device to fit over a person's extremity comprising:
    (a) a heat retaining flowable material tight container comprising:
        (i) a cylindrical shaped flexible outside wall having an inner surface, an outer surface, and two circular end edges,
        (ii) a cylindrical shaped flexible inside wall having an inner surface, an outer surface, and two circular end edges, the inside wall nested inside the outside wall,
        (iii) sealing means to seal the adjacent end edges of the inside and outside walls forming a cylindrical cavity between the outer surface of the inside wall and the inner surface of the outside wall, wherein the inside wall is heat conductive,
    (b) an opening means providing an opening into the cavity to allow it to be filled with warm heat retaining flowable material, sealably closed, opened, and emptied, and
    (c) closure means to detachably close off an end of the cylindrical container.

2. The device of claim 1 wherein the container is water tight.

3. The device of claim 1 wherein the opening means is through the outside wall.

4. The device of claim 1 wherein the opening means comprises a threaded spout and cap.

5. The device of claim 1 wherein the walls are of a polymeric plastic film.

6. The device of claim 5 wherein the film is cloth reinforced.

7. The device of claim 1 wherein the walls are of an elastomeric polymer.

8. The device of claim 1 wherein the container has a lengthwise cut from end to end and lengthwise edges formed by the lengthwise cut, the lengthwise edges being sealed to form a sealed cylindrical cavity with a lengthwise separation, and the device further comprising a closure means to hold the lengthwise edges together along the cut.

9. The device of claim 8 wherein the closure means comprises fabric straps with fabric hook and loop fastening closures to attach the straps across the separation.

10. A method of thermally dilating the vascular system of a person's extremity comprising:
    (A) providing a dilating device comprising
        (a) a heat retaining flowable material tight container comprising:
            (i) a cylindrical shaped flexible outside wall having an inner surface, an outer surface, and two circular end edges,
            (ii) a cylindrical shaped flexible inside wall having an inner surface, an outer surface, and two circular end edges, the inside wall nested inside the outside wall,
(iii) sealing means to seal the adjacent end edges of the inside and outside walls forming a cylindrical cavity between the outer surface of the inside wall and the inner surface of the outside wall,
wherein the composition and the thickness of the inside wall is sufficient to allow heat conduction through the wall, and
(b) an opening means providing a closable opening into the cavity,
(B) filling the device with warm heat retaining flowable material,
(C) expelling air from the cavity out the opening means and closing the opening means,
(D) slipping the device over the extremity,
(E) wrapping the person's hand with a heat insulating fabric,
(F) waiting a sufficient time for the vascular system to dilate, and
(G) removing the device to expose the access to the vascular system.

11. A method of thermally dilating the vascular system of a person's extremity comprising:
(A) providing a dilating device comprising
(a) a heat retaining flowable material tight container comprising:
(i) a cylindrical shaped flexible outside wall having an inner surface, an outer surface, and two circular end edges,
(ii) a cylindrical shaped flexible inside wall having an inner surface, an outer surface, and two circular end edges, the inside wall nested inside the outside wall,
(iii) sealing means to seal the adjacent end edges of the inside and outside walls forming a cylindrical cavity between the outer surface of the inside wall and the inner surface of the outside wall,
wherein the composition and the thickness of the inside wall is sufficient to allow heat conduction through the inside wall, and
(b) an opening means providing a closable opening into the cavity,
(B) filling the device with warm heat retaining flowable material,
(C) expelling air from the cavity out the opening means and closing the opening means,
(D) slipping the device over the extremity,
(E) closing one of the two end edges over the end of the extremity,
(F) waiting a sufficient time for the vascular system to dilate, and
(G) removing the device to expose the access to the vascular system.

* * * * *